United States Patent

Begley et al.

[11] Patent Number: 5,834,604
[45] Date of Patent: Nov. 10, 1998

[54] PHOTOGRAPHIC ELEMENT CONTAINING A COUPLER CAPABLE OF RELEASING A PHOTOGRAPICALLY USEFUL GROUP THROUGH A PYRAZOLE GROUP

[75] Inventors: William James Begley, Webster; Frank Dino Coms; Teh-Hsuan Chen, both of Fairport; Donald Singleton, Jr., Rochester, all of N.Y.

[73] Assignee: Eastman Kodak Company, Rochester, N.Y.

[21] Appl. No.: 923,796

[22] Filed: Sep. 4, 1997

Related U.S. Application Data

[62] Division of Ser. No. 733,372, Oct. 17, 1996, Pat. No. 5,719,071.

[51] Int. Cl.$^6$ ............... C07C 245/06; C07D 231/10; C07D 403/02; G03C 7/305
[52] U.S. Cl. ............... 534/798; 534/DIG. 2; 548/144; 548/217; 548/251; 548/261; 548/374.1
[58] Field of Search ............... 534/798, DIG. 2; 548/374.1, 144, 251, 217, 261

[56] References Cited

U.S. PATENT DOCUMENTS

| 4,861,701 | 8/1989 | Burns et al. | 430/543 |
| 5,283,340 | 2/1994 | Begley et al. | 548/144 |

FOREIGN PATENT DOCUMENTS

| 0 438 129 A3 | 7/1991 | European Pat. Off. |
| 0 499 279 A1 | 8/1992 | European Pat. Off. |
| 60-229030 | 11/1985 | Japan | 430/955 |

*Primary Examiner*—Fiona T. Powers
*Attorney, Agent, or Firm*—Sarah Meeks Roberts

[57] ABSTRACT

A photographic element comprising a support having situated thereon at least one silver halide emulsion layer, the element further comprising a photographic coupler represented by the formula $$\text{COUP}-(T^1)_b-T^2-(T^3)_c-\text{PUG}$$

wherein the substituents are as defined in the specification.

2 Claims, No Drawings

PHOTOGRAPHIC ELEMENT CONTAINING A COUPLER CAPABLE OF RELEASING A PHOTOGRAPICALLY USEFUL GROUP THROUGH A PYRAZOLE GROUP

This is a divisional of application Ser. No. 08/733,372, filed Oct. 17, 1996 now U.S. Pat. No. 5,719,071.

FIELD OF THE INVENTION

This invention relates to photographic elements, processes and couplers, the couplers being of the type that release a photographically useful group (PUG) through a timing or linking group upon reaction with oxidized color developing agent during processing.

BACKGROUND OF THE INVENTION

Various ways are recognized in the photographic industry for releasing a PUG from a compound, such as a coupler, in a photographic material and process. Release can be direct, for example upon reaction of the coupler with oxidized color developing agent during processing, or it can be indirect through a linking or timing group. Linking and timing groups provide the ability to control the timing and rate of release of a PUG in a photographic element, as well as the rate and distance of diffusion of the PUG in the element during processing.

U.S. Pat. No. 4,248,962 describes compounds that release a PUG, such as a development inhibitor group, through a timing group which functions by an (intramolecular) nucleophilic displacement reaction. Other examples of compounds that are capable of releasing a PUG are described in U.S. Pat. Nos. 4,409,323 and 4,861,701. In U.S. Pat. No. 4,409,323, compounds are described which release a PUG by a mechanism which involves electron transfer down a conjugated chain. In U.S. Pat. No. 4,861,701, sequences of timing groups are utilized to release a PUG and to provide desirable control over the impact of the PUG on photographic properties.

European Patent Applications 0 499 279 and 0 438 129 describe photographic compounds having a heterocyclic timing nucleus attached to a coupler moiety through an —O—C(O)— or —OCH$_2$— group, or other group capable of releasing the heterocyclic timing nucleus by electron transfer down an unconjugated chain followed by electron transfer down the conjugated chain of the heterocycle.

However, these compounds do not provide a high degree of flexibility in their rate of release of a PUG, or in their synthetic design, as they are limited by the substituent groups on the heterocyclic timing or linking group.

A need exists for a photographic coupler that is synthetically simple to manufacture; that is capable of providing a wide range of release rates depending upon the particular selection of timing or linking groups and the substituents thereon;

and that is stable when stored for prolonged periods, especially under tropical conditions. The coupler which is needed should be capable of releasing a PUG, such as a development inhibitor, providing effects including, for example, the reduction of gradation, the production of a finer color grain, the improvement of sharpness through the so-called edge effect and the improvement of color purity and color brilliance through so-called inter-image effects.

SUMMARY OF THE INVENTION

This invention provides a photographic element comprising a support having situated thereon at least one silver halide emulsion layer, the element further comprising a photographic coupler represented by the formula COUP—(T$^1$)$_b$—T$^2$—(T$^3$)$_c$—PUG wherein
COUP is a coupler moiety having a coupling site to which T$^1$ is attached;

T$^1$ is a timing or linking group which releases from COUP during processing and which functions by electron transfer down a conjugated or unconjugated chain, or by a nucleophilic displacement reaction, to release T$^2$;

T$^2$ is a pyrazole timing or linking group which, after release from T$^1$, functions by a nucleophilic displacement reaction to release T$^3$ or PUG and is represented by the formula:

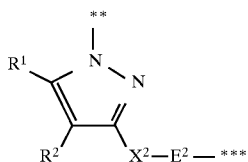

R$^1$ and R$^2$ are independently selected from hydrogen or halogen atoms, or an aliphatic, carbocyclic, carbamoyl, sulfamoyl, carbonamido, sulfonamido, alkoxycarbonyl, alkyl or arylketo, alkyl or arylsulfo, sulfo, hydroxy, acyl, nitro, cyano, amino, alkoxy, alkoxyalkyl, aryloxy, aryloxyalkyl, thioalkoxy, thioalkoxyalkyl, thioaryloxy, thioaryloxyalkyl or heterocyclic group, or R$^1$ and R$^2$, or R$^2$ and X$^2$ or E$^2$ may be bonded together to form a 5, 6, or 7 membered ring;

X$^2$ is a linking group which spatially relates a nitrogen atom of the pyrazole ring and E$^2$ so that upon displacement of T$^2$ from T$^1$, T$^2$ undergoes a nucleophilic displacement reaction with the formation of a three to eight membered ring and the cleavage of the bond between E$^2$ and PUG or T$^3$;

E$^2$ is an electrophilic group which is attached to T$^3$ or PUG and which is displaced therefrom by said nucleophilic displacement reaction after T$^2$ is displaced from T$^1$;

T$^3$ is a timing or linking group attached to E$^2$ which is released therefrom after T$^2$ releases from T$^1$, and which functions by electron transfer down a conjugated or unconjugated chain, or by a nucleophilic displacement reaction, to release PUG;

b and c are independently selected from 0 or 1; and

PUG is a photographically useful group.

Also provided in accordance with the present invention is a process of forming an image in an exposed photographic silver halide element containing a coupler as described above comprising developing the element with a color photographic silver halide developing agent. This invention further provides a coupler as described above.

The invention provides the opportunity to achieve improved image modification in photographic elements through the use of a new type of coupler in a silver halide photographic element, which coupler is capable of releasing a PUG upon photographic processing. The new coupler is synthetically simple to manufacture and provides improved release rates over previously known PUG releasing couplers containing a heterocyclic timing or linking group. The coupler provides greater flexibility in the selection of timing or linking groups and the substituents thereon, and is stable under various types of storage conditions. The coupler utilized in the invention, particularly when PUG is a development inhibitor, provides improved interlayer interimage effects and acutance levels in photographic elements in which it is contained.

DETAILED DESCRIPTION OF THE INVENTION

In the photographic coupler utilized in the present invention, the coupler moiety, as represented by COUP, can be any moiety that will react with oxidized color developing agent during processing to cleave the bond between $T^1$ or $T^2$ and the coupler moiety. The coupler moiety as described herein includes conventional coupler moieties employed to yield both colorless and colored products upon reaction with oxidized color developing agents. Both types of coupler moieties are well known to those skilled in the photographic art and are exemplified in, for example, *Research Disclosure*, September 1994, Item 36544, all published by Kenneth Mason Publications, Ltd., Dudley Annex, 12a North Street, Emsworth, Hampshire PO10 7DQ, ENGLAND.

The coupler moiety can be ballasted or unballasted, and if unballasted, the dye formed upon oxidative coupling is capable of diffusing throughout, or being washed out of, the photographic element (also known as a washout coupler). The coupler can be monomeric, or it can be part of a dimeric, oligomeric or polymeric coupler, in which case more than one PUG can be contained in the coupler. The coupler can also form part of a bis compound in which the PUG forms part of a link between two coupler moieties.

Representative coupler moieties suitable for use in the invention are as follows:

A. Couplers which form cyan dye upon reaction with oxidized color developing agent are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturubersicht," published in Agfa Mitteilungen, Band III, pp. 126–175 (1961), all of which are incorporated herein by reference.

Preferably such cyan dye-forming couplers are phenols and naphthols.

B. Couplers which form magenta dye upon reaction with oxidized color developing agent are described in such representative patents and publications as: U.S. Pat. Nos. 2,600,788; 2,369,489; 2,343,703; 2,311,082; 3,152,896; 3,519,429; 3,062,653; 2,908,573 and "Farbkuppler-eine Literaturubersicht," published in Agfa Mitteilungen,Band III, pp. 126–156 (1961), all of which are incorporated herein by reference.

Preferably such magenta dye-forming couplers are pyrazolones or pyrazolotriazoles. Such couplers are utilized in one preferred embodiment of this invention.

C. Couplers which form yellow dye upon reaction with oxidized color developing agent are described in such representative patents and publications as: U.S. Pat. Nos. 2,875,057; 2,407,210; 3,265,506; 2,298,443; 3,048,194; 3,447,928 and "Farbkuppler-eine Literaturubersicht," published in Agfa Mitteilungen, Band III, pp. 112–126 (1961), all of which are incorporated herein by reference.

Preferably such yellow dye-forming couplers are acylacetamides, such as benzoylacetamides and pivaloylacetamides.

D. Couplers which form a colorless product upon reaction with oxidized color developing agent are described in such representative patents as: U.K. Patent No. 861,138; and U.S. Pat. Nos. 3,632,345; 3,928,041; 3,958,993 and 3,961,959, all of which are incorporated herein by reference.

Specific representative examples of coupler moieties suitable for use in the invention are as follows:

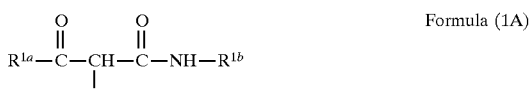
Formula (1A)

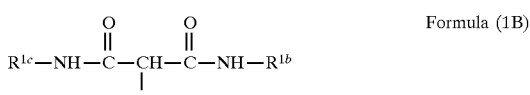
Formula (1B)

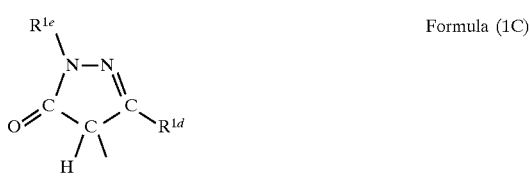
Formula (1C)

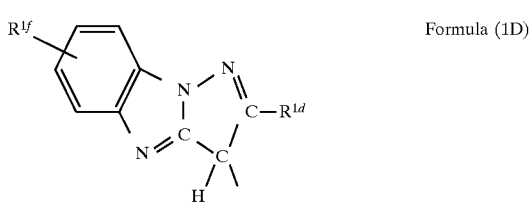
Formula (1D)

Formula (1E)

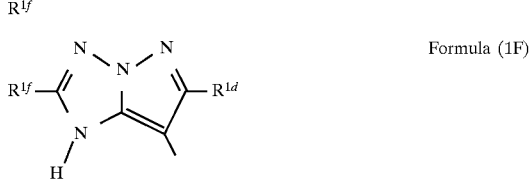
Formula (1F)

Formula (1G)

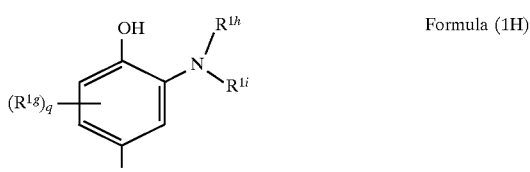
Formula (1H)

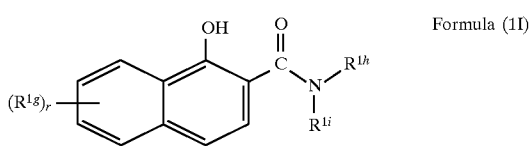
Formula (1I)

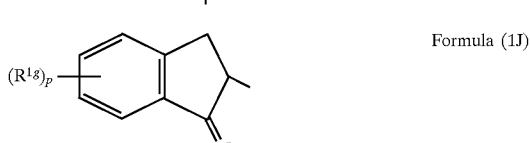
Formula (1J)

Formula (1K)

p in the above formulae can be 0 to 4; q can be 0 to 3; and r can be 0 to 5. The free bond in each of the coupler moieties described above represents the coupling site, which is the position to which the coupling-off group is linked. In the above formulae, $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, or $R^{1k}$ may contain one or more solubilizing groups which will enable the coupler, upon reaction with oxidized color developing agent, to washout of the photographic element. Additionally, $R^{1h}$ and $R^{1i}$ can be a hydrogen. Such groups, and couplers containing them, are exemplified in U.S. Pat. Nos. 4,482,629; 5,026,628; 5,151,343; 5,250,398; and 5,250,399, which are incorporated herein by reference. Specifically preferred solubilizing groups are selected from a carboxyl, sulfo, carbonamido or hydroxyl group, or salt thereof. It is preferred that when a solubilizing group is present, the coupler moiety is also unballasted so that complete washing out of the dye can occur. By unballasted, it is meant that each $R^{1a}$ to $R^{1k}$ contain no more than 20 carbon atoms, preferably no more than 12 carbon atoms, and optimally no more than 8 carbon atoms.

$R^{1a}$ to $R^{1k}$, p, q and r in formulae (1A) to (1K) are set forth in more detail as follows. Each of $R^{1a}$ to $R^{1k}$ is independently selected from the group consisting of a substituted or unsubstituted aliphatic, carbocyclic or heterocyclic group. Aliphatic, carbocyclic, and heterocyclic groups as used herein and elsewhere in this specification are defined in accordance with the definitions set forth in Grant and Hackh's *Chemical Dictionary*, fifth ed., McGraw-Hill 1987, and are in accordance with general rules of chemical nomenclature. The following descriptions of exemplary aliphatic, carbocyclic and heterocyclic groups are intended to be utilized throughout this specification unless specifically noted otherwise.

Exemplary aliphatic groups include alkyl, alkene, and alkyne groups, particularly those having 1 to 25 carbon atoms. Examples of useful groups include methyl, ethyl, propyl, butyl, pentyl, hexyl, octyl, nonyl, decyl, dodecyl, hexadecyl, octadecyl, isopropyl, t-butyl, butenyl, pentenyl, hexenyl, octenyl, dodecenyl, propynyl, butynyl, pentynyl, hexynyl, and octynyl.

Exemplary carbocyclic groups (which include aryl groups) are those having a cyclic portion of 4 to 10 carbon atoms. Examples of useful groups include phenyl, tolyl, naphthyl, cyclohexyl, cyclopentyl, cyclohexenyl, cycloheptatrienyl, cyclooctatrienyl, cyclononatrienyl, cyclopentenyl, anilinyl, and anisidinyl.

Exemplary heterocyclic groups (which include heteroaryl groups) are those in which the cyclic portion has 5 to 10 atoms. Examples of useful groups include pyrrolyl, furyl, tetrahydrofuryl, pyridyl, picolinyl, piperidinyl, morpholinyl, thiadiazolyl, thiatriazolyl, benzothiazolyl, benzoxazolyl, benzimidazolyl, benzoselenozolyl, indazolyl, quinolyl, quinaldinyl, pyrrolidinyl, thiophenyl, oxazolyl, thiazolyl, imidazolyl, selenazolyl, tellurazolyl, triazolyl, tetrazolyl, oxadiazolyl, thienyl, pryanyl, chromenyl, isothiazolyl, isoxazolyl, pyrazinyl, pyrimidinyl, pyridazinyl, indolyl, purinyl, isoquinolyl, quinoxalinyl, and quinazolinyl. Preferred heteroatoms are nitrogen, oxygen, and sulfur.

It is understood throughout this specification and claims that any reference to a substituent by the identification of a group or a ring containing a substitutable hydrogen (e.g., alkyl, amine, aryl, alkoxy, heterocyclic, etc.), unless otherwise specifically described as being unsubstituted or as being substituted with only certain substituents, shall encompass not only the substituent's unsubstituted form but also its form substituted with any substituents which do not negate the advantages of this invention. Also, reference to heterocyclic groups includes attachment at any position on the heterocycle. The term lower alkyl used herein means 1 to 5 carbon atoms. The term aryl or heterocyclic group or ring, unless otherwise indicated, includes bicyclic or other fused rings. Groups suitable for substitution, which may themselves be substituted, include, but are not limited to, alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen groups, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), carbamoyl or carbonamido group, sulfonamido or sulfamoyl groups, ureido groups, acyloxy groups (for example, acetoxy, benzoxy), carboxy groups, cyano groups, sulfo groups, nitro groups and amino groups.

Preferred coupler moieties suitable for the couplers utilized in the invention are represented by

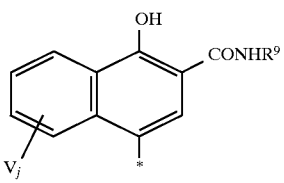

wherein * denotes the coupling site to which $T^1$ is attached.

$R^9$ is selected from hydrogen, or an aliphatic, carbocyclic, or heterocyclic group. In one embodiment this is a wash-out coupler and $R^9$ is preferably hydrogen, an alkyl group containing 1 to 5 carbon atoms, an aryl group containing 6 to 10 carbon atoms or a heterocyclic group containing 4 to 8 carbon atoms. In another embodiment $R^9$ is a ballast group which may contain the above groups V is independently selected from an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio, group; and preferably from an alkyl containing 1 to 5 carbon atoms or a carbamoyl, sulfanoyl, carbonamido, sulfonamido, sulfo, nitro, hydroxyl, carboxyl, amino, alkoxy or alkoxycarbonyl group. j is 0, 1, 2, 3, or 4, preferably 0 or 1.

Also preferred are coupler moieties represented by

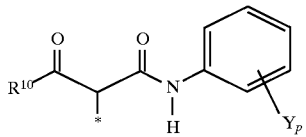

wherein * denotes the coupling site to which $T^1$ is attached.

$R^{10}$ is selected from an aliphatic, carbocyclic, or heterocyclic group; and preferably from an alkyl group containing 1 to 10 carbon atoms, an aryl group containing 6 to 10 carbon atoms or a heterocyclic group containing 4 to 10 carbon atoms;

Y is independently selected from an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy or arylthio group. In one embodiment the coupler is preferably a wash-out coupler and Y is preferably an alkyl group containing 1 to 5 carbon atoms, carbamoyl, sulfamoyl, carbonamido, sulfonamido, sulfo, nitro, hydroxyl, carboxyl, amino, alkoxy or alkoxycarbonyl group. p is 0, 1, 2, 3, or 4, preferably 1 or 2. In another embodiment Y is a ballast group which may contain the above groups.

Other preferred coupler moieties are represented by

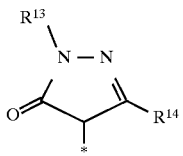

wherein * denotes the coupling site to which $T^1$ is attached.

$R^{13}$ and $R^{14}$ are independently selected from a hydrogen atom, or an aliphatic, carbocyclic, heterocyclic, carbamoyl, sulfamoyl, carbonamido, sulfonamido, acyl, alkylsulfonyl, arylsulfonyl, alkylketo, arylketo, alkoxycarbonyl, aryloxycarbonyl, nitro, cyano, amino, alkoxy, alkoxyalkyl, aryloxy, aryloxyalkyl, thioalkoxy, thioalkoxyalkyl, thioaryloxy, or thioaryloxyalkyl group.

When $R^{14}$ is an amino group, preferred couplers are represented by

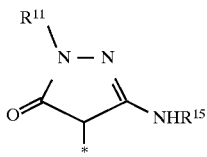

wherein $R^{15}$ an aliphatic, carbocyclic, or heterocyclic group.

The photographic coupler utilized in the invention reacts (i.e. couples) with the oxidized product of a color developing agent during processing to release $(T^1)_b$—$T^2$—$(T^3)_c$—PUG.

$T^1$ and $T^3$ function as described below to release $T^2$ and PUG respectively. $T^2$ is a pyrazole linking or timing group. In this application reference is made to N-1 and N-2 of the pyrazole linking or timing group $T^2$. N-1 is the first nitrogen atom of the pyrazole ring to which $T^1$ or COUP is attached. N-2 is the second nitrogen atom which, after release of $T^2$ from $T^1$, is the nucleophile $Nu^2$, which attacks $E^2$ to release $T^3$ or PUG.

The timing or linking group $T^2$ is shown by the formula

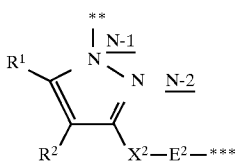

wherein  denotes the point of attachment to $T^1$ and * denotes the point of attachment to $T^3$ or PUG;

Once released from $T^1$, $T^2$ undergoes a nucleophilic reaction to release $T^3$ or PUG. This nucleophilic reaction is brought about when electron density shifts from the first nitrogen atom N-1, of the pyrazole ring, onto the second nitrogen atom N-2, which then acts as a nucleophile to attack the electrophile $E^2$ resulting in cleavage of the bond between $T^2$ and $T^3$, when c is 1 or between $T^2$ and PUG, when c is 0. $T^2$ provides more flexibility to the coupler because both the ring and the X group may be substituted.

$R^1$ and $R^2$ are independently selected from hydrogen or halogen atoms, or an aliphatic, carbocyclic, carbamoyl, sulfamoyl, carbonamido, sulfonamido, alkoxycarbonyl, alkyl or arylketo, alkyl or arylsulfo, sulfo, hydroxy, acyl, nitro, cyano, amino, alkoxy, alkoxyalkyl, aryloxy, aryloxyalkyl, thioalkoxy, thioalkoxyalkyl, thioaryloxy, thioaryloxyalkyl or heterocyclic group, or $R^1$ and $R^2$, or $R^2$ and $X^2$ or $E^2$ may be bonded together to form a 5, 6, or 7 membered ring.

Preferably $R^1$ and $R^2$ are independently hydrogen or halogen atoms, aliphatic groups of 1 to 3 carbon atoms, or carbamoyl or sulfamoyl groups.

$T^1$ and $T^3$ can be any timing or linking groups known in the art, for instance those described below and in U.S. Pat. Nos. 4,248,962; 4,409,323; 4,421,845; 4,857,447; 4,861,701; 4,864,604; 4,886,736; 4,891,304; 5,034,311; 5,055,385; 5,190,846; and European Patent Application 0 167 168, all of which 15 are incorporated herein by reference. Thus, they independently may be timing or linking groups which function by nucleophilic displacement reaction (of the type described in, for example U.S. Pat. No. 4,248,962) or electron transfer down a conjugated chain (of the type described in, for example, U.S. Pat. No. 4,861,701). They may also be timing or linking groups which function by electron transfer down an unconjugated chain. These last groups are known in the art under various names. Often they have been referred to as groups capable of utilizing a hemiacetal or iminoketal cleavage reaction or groups capable of utilizing a cleavage reaction due to ester hydrolysis. Regardless of their label, though, their mechanism is that of electron transfer down an unconjugated chain which results, typically, in a relatively fast decomposition and the production of carbon dioxide, formaldehyde or other low molecular weight by-products. The groups are exemplified specifically in European Patent Application 0 464 612 and 0 523 451, both of which are incorporated herein by reference.

As used herein, "nucleophilic displacement reaction" means a reaction in which a nucleophilic center of a compound reacts directly, or indirectly, through an intervening molecule, with another site on the compound (an electrophilic center) to effect displacement of a group or atom attached to the electrophilic center. Such compounds have a nucleophilic group and electrophilic group spacially related by the configuration of the molecule to promote reactive proximity. The electrophilic group and the nucleophilic group are located in the coupling-off group as described so that a cyclic organic ring, or a transient cyclic organic ring can be easily formed by an intramolecular reaction involving the nucleophilic center and the electrophilic center.

A nucleophilic group is understood to be a grouping of atoms, one of which is electron rich. This atom is referred to as the nucleophilic center, representative examples of which include oxygen, sulfur and nitrogen atoms. An electrophilic group is understood to be a grouping of atoms, one or more of which is electron deficient. This atom(s) is referred to as the electrophilic center, representative examples of which include carbonyl, thiocarbonyl, phosphinyl, and thiophosphinyl. Additional examples of nucleophilic groups, electrophilic groups and linking groups (to be discussed below) can be found in U.S. Pat. No. 4,248,962, incorporated herein by reference.

In one preferred embodiment of the invention, $T^1$ is a timing or linking group which functions by electron transfer down an unconjugated chain and $T^3$ is a timing or linking group which functions by electron transfer down a conjugated chain.

In another preferred embodiment of the invention, $T^1$ is a timing or linking group which functions by electron transfer down an unconjugated chain and $T^3$ is a timing or linking group which functions by nucleophilic displacement reaction.

In another preferred embodiment of the invention, $T^1$ and $T^3$ are timing or linking groups which function by nucleophilic displacement reactions. $T^1$ and $T^3$ may be the same or different.

In embodiments which involve nucleophilic displacement reactions of the timing or linking groups $T^1$, $T^2$ or $T^3$, subsequent discussions of the timing and linking groups will make reference to nucleophilic groups $Nu^1$ and $Nu^3$, linking groups $X^1$, $X^2$, and $X^3$, and electrophilic groups $E^1$, $E^2$, and $E^3$. When describing $T^1$, $Nu^1$, $X^1$ and $E^1$ will be used; when describing $T^2$, $X^2$ and $E^2$ will be used; and when describing $T^3$, $Nu^3$, $X^3$ and $E^3$ will be used. $Nu^1$ may be the same or different from $Nu^3$; $X^1$, $X^2$, and $X^3$ may be the same or independently different from each other; and $E^1$, $E^2$, and $E^3$ may be the same or independently different from each other. Representative examples of nucleophilic groups, electrophilic groups and linking groups can be found in U.S. Pat. No. 4,248,962, previously incorporated by reference.

$T^1$ in these embodiments thus comprises a nucleophilic group ($Nu^1$)—which is attached to the coupling site of COUP and which is displaced therefrom upon reaction of COUP with oxidized color developing agent during processing—and an electrophilic group ($E^1$)—which is attached to N-1, the first nitrogen atom of the pyrazole moiety $T^2$, and which is displaced therefrom by $Nu^1$ after $Nu^1$ is displaced from COUP.

$T^2$ comprises a pyrazole moiety with a masked nucleophilic group (N-2, the second nitrogen atom of the pyrazole ring)—which acts only as a nucleophile when $T^2$ is released from $T^1$ upon cleavage of the bond between $E^1$ and N-1, the first nitrogen atom of the pyrazole ring—and an electrophilic group ($E^2$)—which is attached to $T^3$ and which is displaced therefrom by N-2 after N-2 is unmasked as a nucleophile.

$T^3$ in these embodiments comprises a nucleophilic group ($Nu^3$)—which is attached to the electrophilic group $E^2$ of $T^2$ and which is displaced therefrom upon cleavage of the bond between $E^1$ and N-1, subsequent unmasking of N-2 as a nucleophile, and cleavage of the bond between $E^2$ and ($Nu^3$)—and an electrophilic group ($E^3$)—which is attached to the PUG and which is displaced therefrom by $Nu^3$ after $Nu^3$ is displaced from $T^2$.

The nucleophilic and electrophilic groups in $T^1$, $T^2$ and $T^3$ are separated from each other by linking groups ($X^1$ in $T^1$, $X^2$ in $T^2$ and $X^3$ in $T^3$). The linking group $X^1$ spatially relates the nucleophilic group $Nu^1$ from the electrophilic group $E^1$ so that upon displacement of the nucleophilic group from the coupler moiety, $T^1$ undergoes a nucleophilic displacement reaction with the formation of, preferably, a three to eight membered ring and the cleavage of the bond between the electrophilic group $E^1$ and $T^2$.

The linking group $X^2$ spatially relates the nucleophilic group N-2 of the pyrazole moiety, from the electrophilic group $E^2$ so that upon displacement of the pyrazole moiety and unmasking of the nucleophilic group from $T^1$, $T^2$ undergoes a nucleophilic displacement reaction with the formation of, preferably, a three to eight membered ring fused to the pyrazole moiety and cleavage of the bond between the electrophilic group $E^2$ and the nucleophilic group $Nu^3$. Suitable $X^2$ linking groups include 1,2-phenylene, 1,2-naphthelene, pyrindylene and —[($R^3$ ($R^4$) C]— as hereafter defined. Suitable $E^2$ electrophilic groups include —N($R^7$)C(O)— as hereafter defined.

The linking group $X^3$ spatially relates the nucleophilic group $Nu^3$, from the electrophilic group $E^3$ so that upon displacement of the nucleophilic group from $T^2$, $T^3$ undergoes a nucleophilic displacement reaction with the formation of, preferably, a three to eight membered ring and the cleavage of the bond between the electrophilic group $E^3$ and the PUG.

Preferred couplers utilized in the invention when $T^1$ functions by electron transfer down an unconjugated chain and $T^3$ functions by electron transfer down a conjugated chain are represented by the formula:

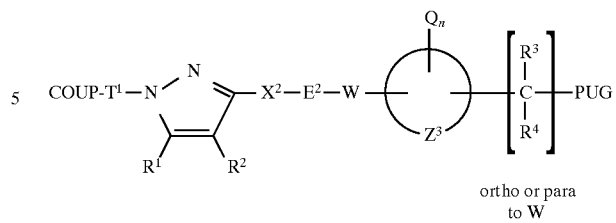

ortho or para to W wherein COUP, $X^2$, $E^2$ $R^1$ and $R^2$ and PUG are as defined previously.

In one embodiment $T^1$ is a timing or linking group which functions by electron transfer down an unconjugated chain and is of the formula

wherein * denotes the point of attachment of $T^1$ to COUP and ** denotes the point of attachment to $T^2$. $Z^1$ is oxygen, sulfur or an unsubstituted or lower alkyl ($C_1$–$C_5$) substituted nitrogen. $L^1$ is a bivalent group selected from;

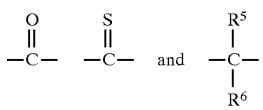

where $R^5$ and $R^6$ are independently a hydrogen, alkyl or an aryl group and are preferably hydrogen.

Preferably $T^1$ is selected from:

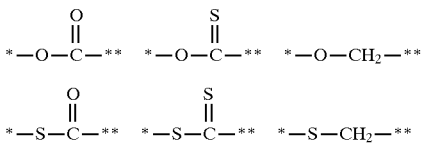

More preferably, $T^1$ is selected from:

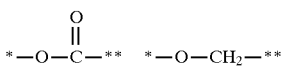

$T^3$ is represented by the formula

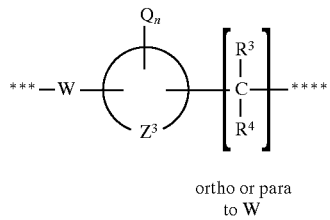

ortho or para to W wherein *** denotes the point of attachment to $E^2$ and
**** denotes the point of attachment to PUG.

W is oxygen, sulfur or an unsubstituted or lower alkyl ($C_1$–$C_5$) substituted nitrogen. Q is independently selected from an alkyl, carbocylic, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio group. $Z^3$ represents the atoms necessary to complete a mono or bicyclic aromatic or heterocyclic ring system containing 5 to 10 ring atoms. —C($R^3$)($R^4$)— is in a favorable position relative to W, ortho or para, to allow for the conjugated transfer of electron density from W to —C($R^3$)($R^4$)— and cleavage of the bond between $T^3$ and PUG. Preferably $Z^3$ is a phenyl group. $R^3$ and $R^4$ are independently selected from hydrogen, or an aliphatic, carbocyclic, or heterocyclic group, or $R^3$ and $R^4$, or $R^3$ or $R^4$ and $Z^3$ together may form a 5, 6, or 7 membered carbocyclic or heterocyclic ring. By 5, 6 or 7 membered ring it is meant any of the carbocyclic or heterocyclic rings previously described that comprise the requisite number of carbon atoms in their ring structure. $R^3$ and $R^4$ are preferably independently selected from hydrogen or an alkyl having from 1 to 8 carbon atoms. n is 0, 1, 2 or 3.

Couplers utilized in another embodiment of the invention in which $T^1$ functions by electron transfer down an unconjugated chain and $T^3$ functions by a nucleophilic displacement reaction can be represented by the formula

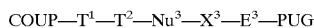

COUP—$T^1$—$T^2$—$Nu^3$—$X^3$—$E^3$—PUG wherein COUP, $T^1$, $T^2$, and PUG are as defined previously. $T^3$ is represented by the formula

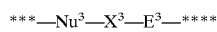

*—$Nu^3$—$X^3$—$E^3$—** wherein * denotes the point of attachment to $E^2$ and ** denotes the point of attachment to PUG.

$Nu^3$ is a nucleophilic group which is attached to $T^2$ and which is displaced therefrom upon cleavage of the bond between $T^1$ and $T^2$. $X^3$ is a linking group for spatially relating $Nu^3$ and $E^3$ so that upon displacement of $Nu^3$ from $T^2$, $Nu^3$—$X^3$—$E^3$ ($T^3$) undergoes a nucleophilic displacement reaction with the formation of a three to eight membered ring and the cleavage of the bond between $E^3$ and the PUG. $E^3$ is an electrophilic group which is attached to the PUG and which is displaced therefrom by $Nu^3$ after $Nu^3$ is displaced from $T^2$.

The preferred couplers utilized in this embodiment of the invention are represented by the formula:

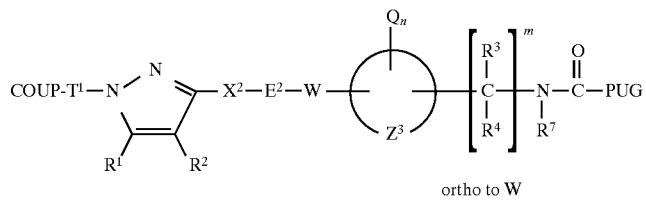

ortho to W wherein COUP, $T^1$, $X^2$, $E^2$, $R^1$, $R^2$, $R^3$, $R^4$ and PUG are as previously defined and wherein $Nu^3$—$X^3$—$E^3$ ($T^3$) is represented by the formula

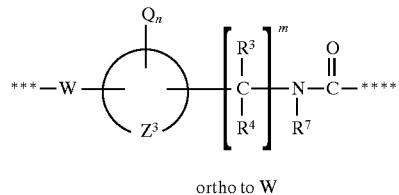

ortho to W wherein W is oxygen, sulfur or an unsubstituted or lower alkyl substituted nitrogen. Q is independently selected from an alkyl, carbocylic, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio group. $Z^3$ represents the atoms necessary to complete a mono or bicyclic aromatic or heterocyclic ring system containing 5 to 10 ring atoms. —C($R^3$)($R^4$)— is in a position ortho to W. In the above structures, the term "ortho to W" refers to a favorable spatial relationship for nucleophilic attack of the nucleophilic group W, in this instance, on the electrophilic group —N($R^7$)—C(O)—. $R^3$ and $R^4$ are ortho to W. $R^3$ and $R^4$ are independently selected from hydrogen, or an aliphatic, carbocyclic, or heterocyclic group, or $R^3$ and $R^4$, or $R^3$ or $R^4$ and $Z^3$ together may form a 5, 6, or 7 membered carbocyclic or heterocyclic ring. $R^3$ and $R^4$ are preferably independently selected from hydrogen or an alkyl having from 1 to 8 carbon atoms.

$R^7$ is selected from hydrogen, or an aliphatic, carbocyclic, or hetercyclic group, and two of $R^3$, $R^4$, $Z^3$ and $R^7$ may be bonded together in a pair to form a 5, 6 or 7 membered ring. More preferably $R^7$ is hydrogen; alkyl groups of 1 to 5 carbon atoms or a substituted aryl. By a 5, 6 or 7 membered ring it is meant any of the carbocyclic or heterocyclic rings previously described that comprise the requisite number of carbon atoms in their ring structure. n and m are independently selected from 0, 1, 2 or 3. m is preferably 0 or 1.

In some suitable embodiments $T^3$ is represented by the formulae

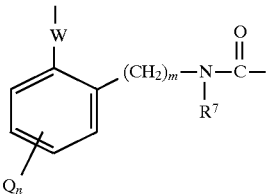

-continued

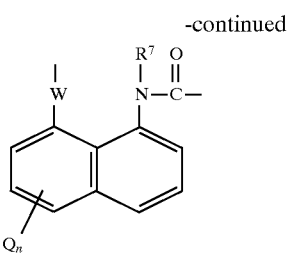

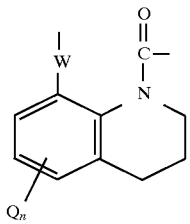

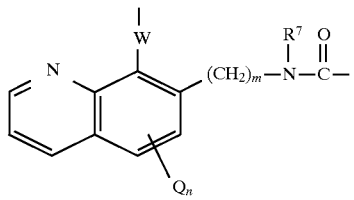

W, Q, n and $R^7$ are as defined above.

Couplers utilized in another embodiment of the invention in which both $T^1$ and $T^3$ function by nucleophilic displacement reactions can be represented by the formula

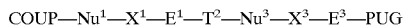

wherein COUP, $T^2$, $Nu^3$, $X^3$, $E^3$ and PUG are as previously defined. $T^1$ is $-Nu^1-X^1-E^1-$. $Nu^1$ is a nucleophilic group which is attached to the coupling site of COUP and which is displaced therefrom upon reaction of COUP with oxidized color developing agent during processing. $X^1$ is a linking group for spatially relating $Nu^1$ and $E^1$ so that upon displacement of $Nu^1$ from COUP, $-Nu^1-X^1-E^1-$ undergoes a nucleophilic displacement reaction with the formation of a three to eight membered ring and the cleavage of the bond between $E^1$ and $T^2$. $E^1$ is an electrophilic group which is attached to $T^2$ and which is displaced therefrom by $Nu^1$ after $Nu^1$ is displaced from COUP. A more preferred embodiment is represented by

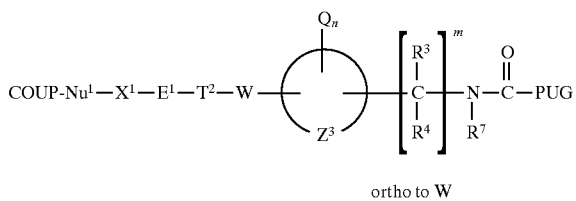

ortho to W wherein COUP, $T^2$, W, n, m, Q, $Z^3$, $R^3$, $R^4$, $R^7$ and PUG are as previously defined.

In addition to the preferred timing and linking groups described above, some other suitable $T^1$ and $T^3$ groups can be selected from the following:

1. Acyclic timing or linking groups capable of nucleophilic displacement reaction:

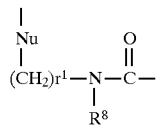

where $r^1$ is 0 to 5; preferably 2, 3 or 4; Nu is a nucleophilic group, typically

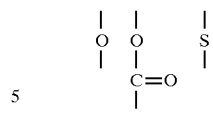

and $R^8$ is hydrogen, or an aliphatic, carbocyclic, or heterocyclic group. Preferably, it is an alkyl of 1 to 20 carbon atoms or aryl of 6 to 20 carbon atoms. More preferably, it is an alkyl of 1 to 4 carbon atoms or an aryl of 6 to 10 carbon atoms.

2. Aromatic timing and linking groups capable of electron transfer down a conjugated chain:

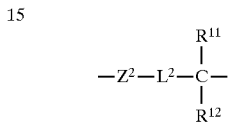

where $Z^2$ is oxygen, sulfur or an unsubstituted or lower alkyl($C^1$–$C_5$) substituted nitrogen; $L^2$ is pyridylene, 1,2- or 1,4-phenylene or naphthalene group; and $R^{11}$ and $R^{12}$ are independently selected from a hydrogen, or an alkyl or aryl group, preferably one containing fewer than 10 carbon atoms.

The coupler utilized in the invention releases a PUG precursor upon coupling during processing. The PUG can be any PUG known in the art. Examples include development inhibitors, bleach accelerators, development accelerators, dyes, bleach inhibitors, couplers, developers, silver complexing agents, fixing agents, image toners, stabilizers, hardeners, tanning agents, fogging agents, ultraviolet radiation absorbers, antifoggants, nucleators, chemical or spectral sensitizers, and desensitizers. Other PUGs known in the art are also possible in the present invention. These PUGs, as well as those specifically described above, can be released from $-(T^1)_b-T^2-(T^3)_c-$ in the form of a precursor which, upon subsequent reaction, such as redox reaction with a component of the developing solution, releases the PUG.

Couplers which release development inhibitors can enhance the effects heretofore obtained with untimed or unlinked DIR couplers since they can release a development inhibitor at a distance from the point at which oxidized color developing agent reacted with the coupler, in which case they can provide, for example, enhanced interlayer interimage effects.

Couplers as described which release bleach inhibitors or bleach accelerators can be employed in the ways described in the photographic art to inhibit the bleaching of silver or accelerated bleaching in areas of a photographic element.

Couplers as described which release a dye or dye precursor can be used in processes where the dye is allowed to diffuse to an integral or separate receiving layer to form a desired image. Alternatively, the dye can be retained in the location where it is released to augment the density of the dye formed from the coupler from which it is released or to modify or correct the hue of that dye or another dye. In another embodiment, the dye can be completely removed from the element and the dye which was not released from the coupler can be retained in the element as a color correcting mask.

Couplers as described in which the PUG is a developing agent can be used to release a developing agent which will compete with the color forming developing agent, and thus reduce dye density.

In the preferred embodiment of the invention the PUG is a development inhibitor. More preferably it is selected from a mercaptotetrazole, mercaptotriazole, dimercaptothiadiazole, mercaptooxadiazoles, mercaptoimidazole, mercaptobenzoimidazole, mercaptobenzoxazole, mercaptobenzothiazole, mercaptothiadiazole, tetrazole, 1,2,3-triazole, 1,2,4-triazole or benzotriazole.

Representative PUGs suitable for use in the present invention can be found in the following references, all of which are incorporated herein by reference: U.S. Pat. Nos. 3,227,554; 3,384,657; 3,615,506; 3,617,291; 3,733,201 and U.K. Pat. No. 1,450,479 (development inhibitors); U.S. Pat. Nos. 3,880,658; 3,931,144; 3,932,380; 3,932,381; 3,942,987, and 4,840,884 (dye and dye precursors); "*On the Chemistry of White Couplers,*" by W. Puschel, Agfa-Gevaert AG Mitteilungen and der Forschungs-Laboratorium der Agfa-Gevaert AG, Springer Verlag, 1954, pp. 352–367; U.S. Pat. Nos. 2,998,314; 2,808,329; 2,689,793; 2,742,832; German Pat. No. 1,168,769 and British Pat. No. 907,274 (couplers); U.S. Pat. Nos. 2,193,015; 2,108,243; 2,592,364; 3,656,950; 3,658,525; 2,751,297; 2,289,367; 2,772,282; 2,743,279; 2,753,256 and 2,304,953 (developing agents); U.S. Pat. Nos. 3,705,801; 3,715,208; and German OLS No. 2,405,279 (bleach inhibitors); U.S. Pat. Nos. 4,912,024; 5,063,145, columns 21–22, lines 1–70; and EP Patent No 0,193,389 (bleach accelerators); and U.S. Pat. Nos. 4,209,580; 4,463,081; 4,471,045; and 4,481,287 and in published Japanese patent application No. 62-123,172 (electron transfer agents). Advantages of DIR couplers are described in, for example, the article by C. R. Barr, J. R. Thirtle and P. W. Vittum entitled "Development-Inhibitor-Releasing (DIR) Couplers in Color Photography" in Photographic Science and Engineering 13, 74(1969).

Specific couplers suitable for use in the invention are as follows:

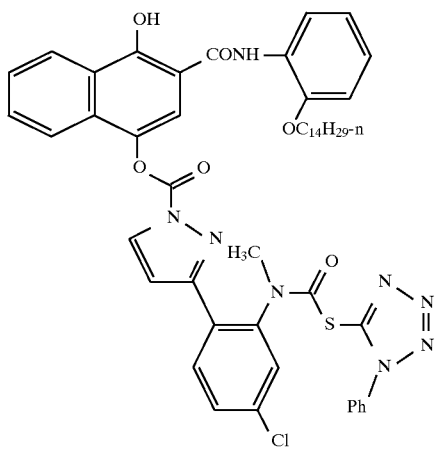

DIR coupler I-1

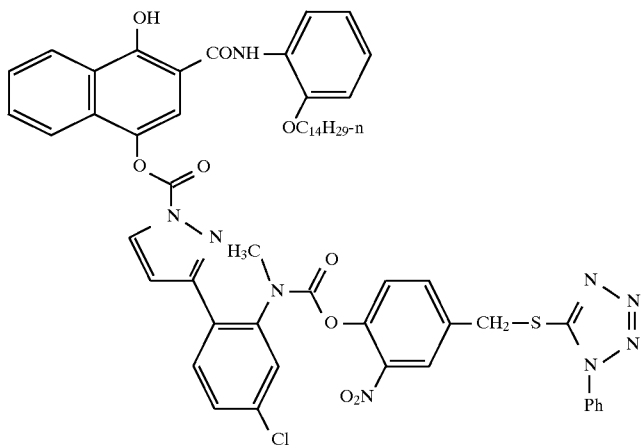

DIR coupler I-2

-continued
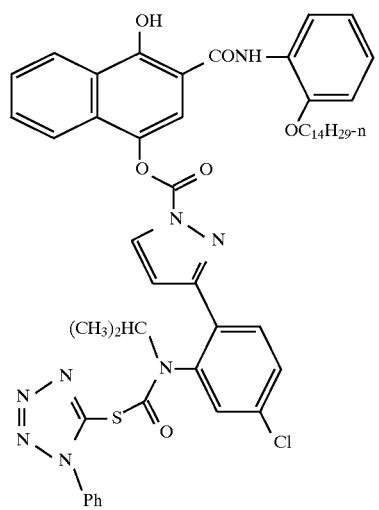
DIR coupler I-3
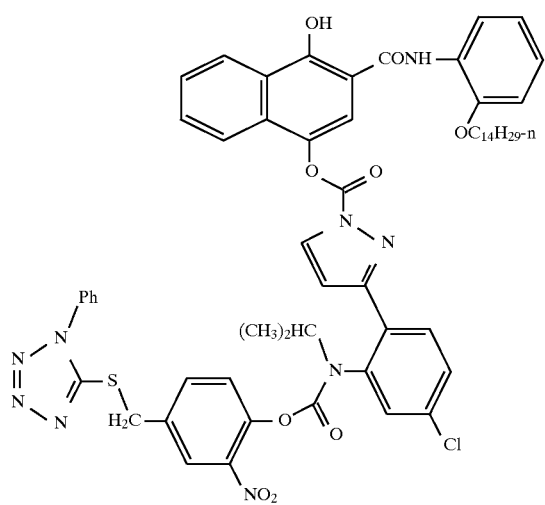
DIR coupler I-4
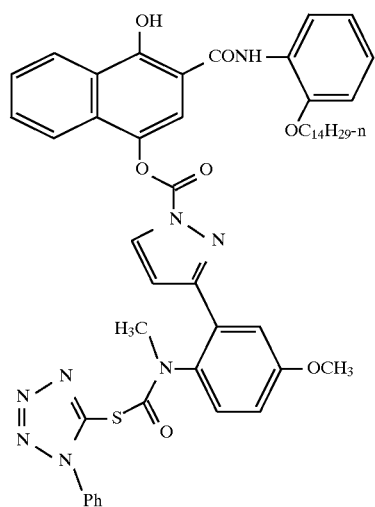
DIR coupler I-5

-continued
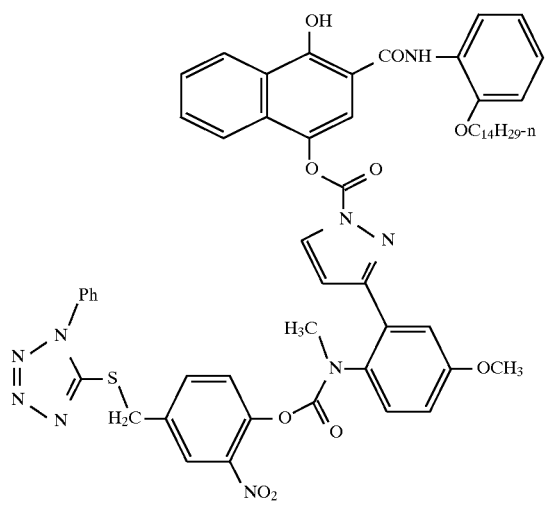
DIR coupler I-6
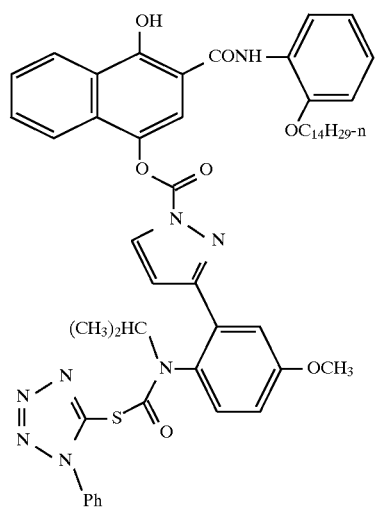
DIR coupler I-7
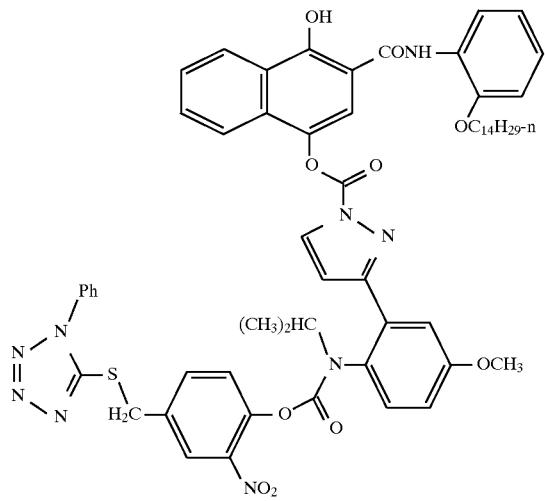
DIR coupler I-8

-continued
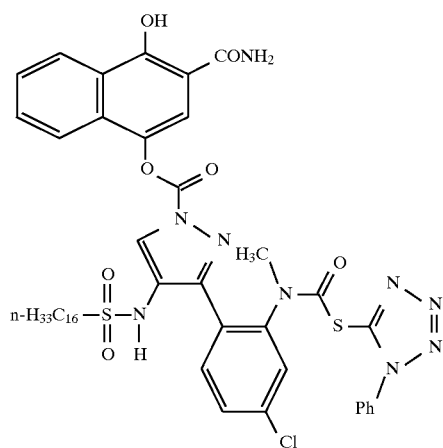
DIR coupler I-9
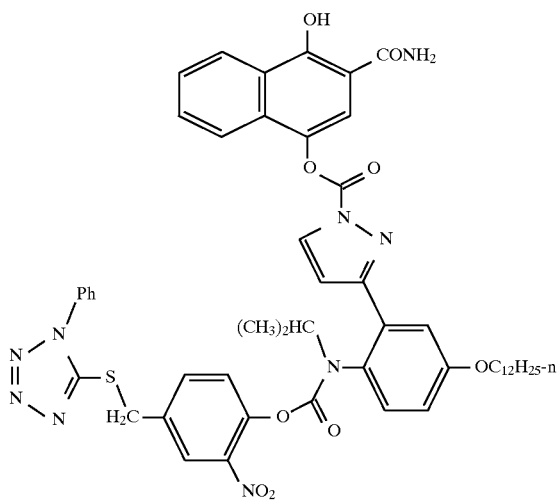
DIR coupler I-10
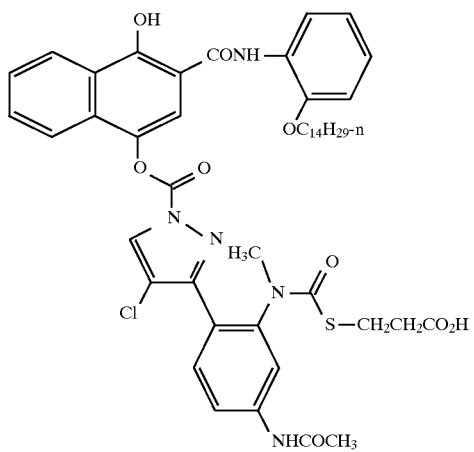
BAR coupler I-11

DIR coupler I-12
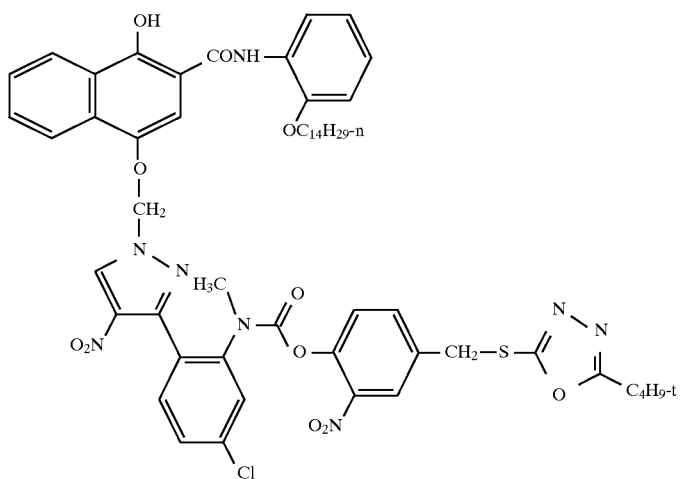
Coupler I-13
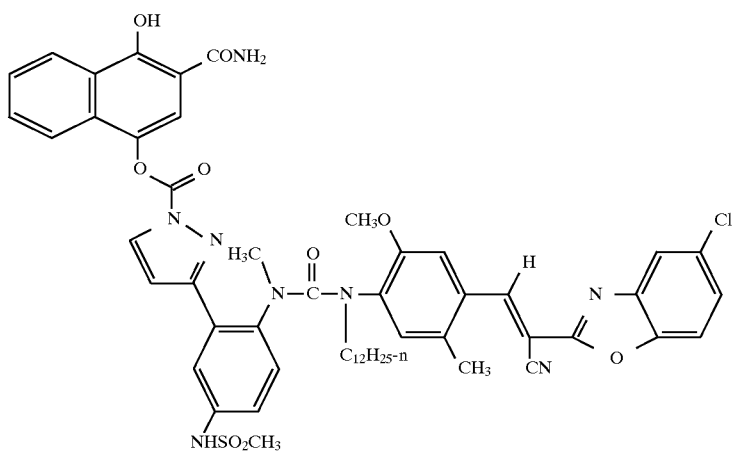
Coupler I-14
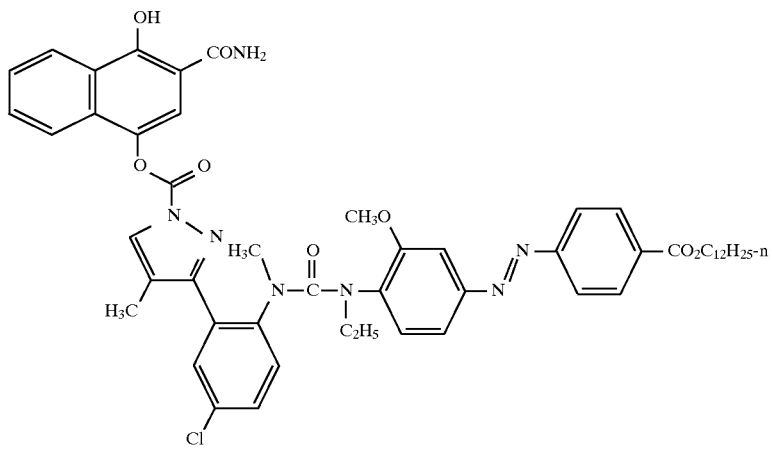

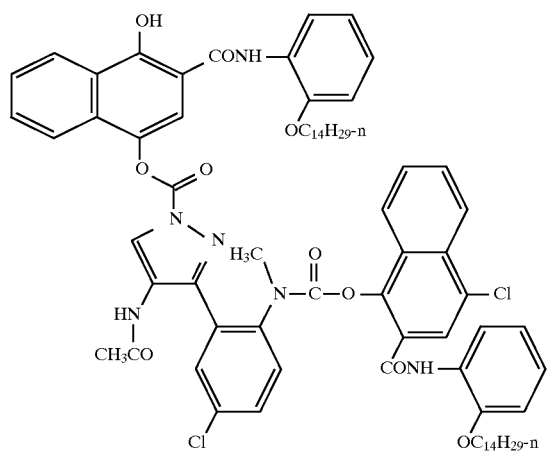
Coupler I-15
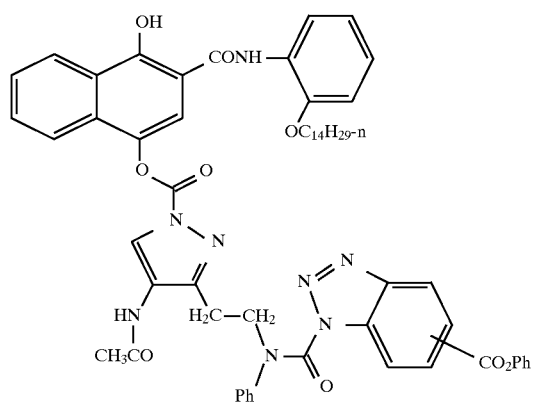
DIR coupler I-16
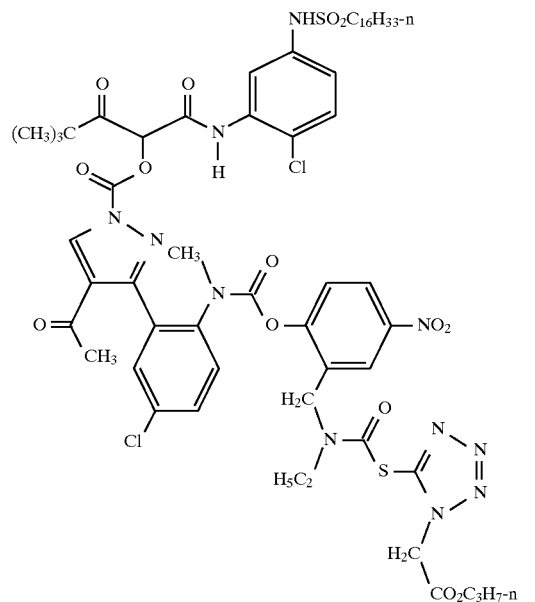
DIR coupler I-17

-continued
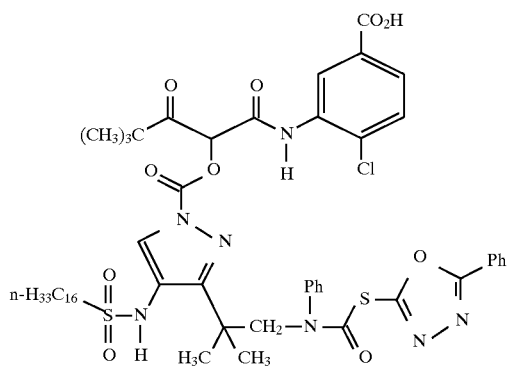
DIR coupler I-18
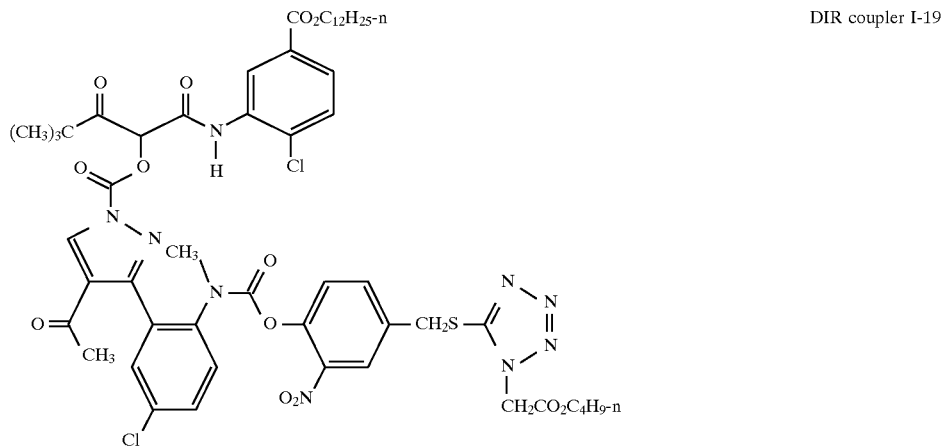
DIR coupler I-19
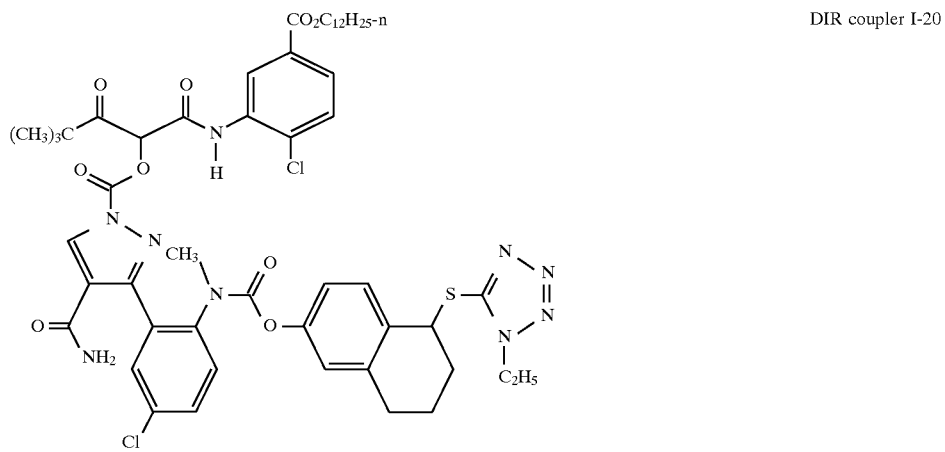
DIR coupler I-20

-continued

DIR coupler I-21

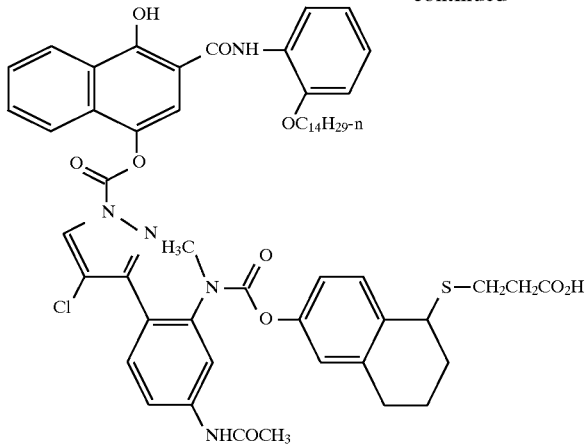

The photographic couplers can be incorporated in photographic elements by means and processes known in the photographic art. Photographic elements in which the couplers are incorporated can be simple elements comprising a support and a single silver halide emulsion layer or multilayer, multicolor elements. The couplers can be incorporated in at least one of the silver halide emulsion layers and/or in at least one other layer, such as an adjacent layer, where they will come into reactive association with oxidized color developing agent which has developed silver halide in the emulsion layer. Preferably the couplers are in a silver halide emulsion layer.

The silver halide emulsion layer can contain or have associated with it other photographic couplers such as dye-forming couplers, colored masking couplers, and/or competing couplers. These other photographic couplers can form dyes of any color and hue. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units or another layer having associated therewith a photographic coupler as described above. Each silver halide emulsion unit can be composed of one or more layers and the various units and layers can be arranged in different locations with respect to one another.

The light sensitive silver halide emulsions can include coarse, regular or fine grain silver halide crystals or mixtures thereof, in a hydrophobic colloid, such as gelatin. The crystals can be comprised of any halide composition such as silver chloride, silver bromide, silver bromoiodide, silver chlorobromide, silver chloroiodide, silver chlorobromoiodide and mixtures thereof. The emulsions can be negative-working or positive-working emulsions and can be incorporated into negative or reversal elements as described in U.S. Pat. Nos. 5,411,839, as well as other types of elements known in the art. They can form latent images predominantly on the surface of the silver halide grains or predominantly on the interior of the silver halide grains. They can be chemically and spectrally sensitized by methods known in the art.

The photographic elements may also contain a transparent magnetic recording layer such as a layer containing magnetic particles on the underside of a transparent support, as described in U.S. Pat. Nos. 4,279,945 and 4,302,523 and in *Research Disclosure*, November 1992, Item 34390 published by Kenneth Mason Publications, Ltd., Dudley Annex, 12a North Street, Emsworth, Hampshire PO10 7DQ, ENGLAND. Typically, the element will have a total thickness (excluding the support) of from about 5 to about 30 microns. Further, the photographic elements may have an annealed polyethylene naphthalate film base such as described in Hatsumei Kyoukai Koukai Gihou No. 94-6023, published Mar. 15, 1994 (Patent Office of Japan and Library of Congress of Japan) and may be utilized in a small format system, such as described in *Research Disclosure*, June 1994, Item 36230 published by Kenneth Mason Publications, Ltd., Dudley Annex, 12a North Street, Emsworth, Hampshire PO10 7DQ, ENGLAND, and such as the Advanced Photo System, particularly the Kodak ADVANTIX films or cameras.

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as with electron beam, beta radiation, gamma radiation, x-ray, alpha particle, neutron radiation, and other forms of corpuscular and wave-like radiant energy in either noncoherent (random phase) forms or coherent (in phase) forms, as produced by lasers. When the photographic elements are intended to be exposed by x-rays, they can include features found in conventional radiographic elements.

The photographic elements are preferably exposed to actinic radiation, typically in the visible region of the spectrum, to form a latent image, and then processed to form a visible dye image. Development is typically followed by the conventional steps of bleaching, fixing, or bleach-fixing, to remove silver or silver halide, washing, and drying.

In the following Table, reference will be made to (1) *Research Disclosure*, December 1978, Item 17643, (2) *Research Disclosure*, December 1989, Item 308119, and (3) *Research Disclosure*, September 1994, Item 36544, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the elements of the invention. The Table and its cited references also describe suitable ways of preparing, exposing, processing and manipulating the elements, and the images contained therein. Photographic elements and methods of processing such elements suitable for use with this invention are described in *Research Disclosure*, February 1995, Item 37038, published by Kenneth Mason Publications, Ltd., Dudley Annex, 12a North Street, Emsworth, Hampshire PO10 7DQ, ENGLAND, the disclosure of which is incorporated herein by reference.

| Reference | Section | Subject Matter |
|---|---|---|
| 1 | I, II | Grain composition, |
| 2 | I, II, IX, X, XI, XII, XIV, XV | morphology and preparation. Emulsion preparation including hardeners, coating |
| 3 | I, II, III, IX A & B | aids, addenda, etc. |
|   | III, IV | Chemical sensitization and |
| 2 | III, IV | spectral sensitization/ |
| 3 | IV, V | desensitization |
| 1 | V |  UV dyes, optical brighteners, |
| 2 | V | luminescent dyes |
| 3 | VI |  |
| 1 | VI | Antifoggants and stabilizers |
| 2 | VI |  |
| 3 | VII |  |
| 1 | VIII | Absorbing and scattering |
| 2 | VIII, XIII, XVI | materials; Antistatic layers; matting agents |
| 3 | VIII, IX C & D |  |
| 1 | VII | Image-couplers and image- |
| 2 | VII | modifying couplers; Wash-out |
| 3 | X | couplers; Dye stabilizers and hue modifiers |
| 1 | XVII | Supports |
| 2 | XVII |  |
| 3 | XV |  |
| 3 | XI | Specific layer arrangements |
| 3 | XII, XIII | Negative working emulsions; Direct positive emulsions |
| 2 | XVIII | Exposure |
| 3 | XVI |  |
| 1 | XIX, XX | Chemical processing; |
| 2 | XIX, XX, XXII | Developing agents |
| 3 | XVIII, XIX, XX |  |
| 3 | XIV | Scanning and digital processing procedures |

Synthetic Examples

The following synthetic examples illustrate the synthesis of couplers suitable for use in the invention. It is intended to be illustrative, and can be readily modified by one of ordinary skill in the art to obtain other suitable couplers.

Synthesis of DIR Coupler I-5

Intermediate A-1

3-(N-Methyl-2'-amino-5'-methoxyphenyl)pyrazole (4.2 g, 20.7 mMole), was dissolved in dry dimethylformamide (50 mL), di-tert-butyl dicarbonate (5.4 g, 24.8 mMole) was added and the resulting solution was stirred under a nitrogen atmosphere at room temperature for 8 hours. Another batch of di-tert-butyl dicarbonate (5.4 g, 24.8 mMole) was added and the reaction was stirred for a further 8 hours. At the end of this period the solvent was removed under reduced pressure and the residue dissolved in ethyl acetate (100 mL). The ethyl acetate solution was washed with water (1×100 mL), then 2N-HCl (1×100 mL), dried over magnesium sulfate, filtered and concentrated under reduced pressure. The resulting oil was taken up in a 50% mixture of ethyl acetate and heptane and quickly passed through a short pad of silica gel using the same solvent mixture as eluant. The eluate was collected, and the solvent removed under reduced pressure to yield intermediate A-1 of sufficient purity for the next step.

Intermediate A-2

Intermediate A-1 (2.8 g, 9.2 mMole), was dissolved in dry tetrahydrofuran (50 mL), to which was added p-nitrophenyl chloroformate (2.05 g, 10.2 mMole), and the resulting solution was stirred under a nitrogen atmosphere for 30 minutes. The solution was then diluted with ethyl acetate (100 mL), and the organic layer washed with 2N-HCl (2×50 mL), dried over magnesium sulfate, filtered and the solvent removed under reduced pressure to give intermediate A-2 as a white foam, yield 4.81 g.

Intermediate A-4

Intermediate A-2 (4.81 g, 10.3 mMole) and 1,4-dihydroxy-N-(2-tetradecyloxy)phenyl-naphthalene-2-carboxamide, A-3, (6.06 g, 12.3 mMole), were dissolved in dichloromethane (50 mL). To this solution was added N,N-diisopropylethylamine (4.4 mL, 25.7 mMole) and the solution was stirred under nitrogen at room temperature for 1 hour. After this period the reaction was diluted with dichloromethane (100 mL), and the dichloromethane solution was washed with 2N-HCl (2×50 mL). The organic layer was then collected, dried over magnesium sulfate, filtered and concentrated under reduced pressure to yield crude product. This crude material was dissolved in a mixture of ethyl acetate:dichloromethane:heptane (5:20:95), and subjected to medium pressure column chromatography over silica gel using the same solvent in the elution. The fraction containg the product was collected and the solvent removed under reduced pressure to give intermediate A-4. Yield 6.2 g.

Intermediate A-5

Intermediate A-4 (6.0 g, 7.3 mMole) was dissolved in dry dichloromethane (100 mL) and treated with trifluoroacetic acid (25 mL), drop by drop. The reaction solution was stirred at room temperature for 30 minutes and then concentrated under reduced pressure to yield an oil. This oil was dissolved in ethyl acetate (100 mL) and washed with 10%-sodium bicarbonate (1×100 mL). The resulting solid was filtered off, washed with diethyl ether and air dried to yield 4.5 g of intermediate A-5.

Intermediate A-6

Intermediate A-5 ( 2.0 g, 2.8 mMole) was slurried in dry tetrahydrofuran (20 mL). To this slurry was added a 20% solution of phosgene in toluene (2.74 mL, 5.5 mMole), whereupon dissolution was achieved. The resulting solution was stirred at room temperature for 15 minutes. The solvent was removed under reduced pressure to yield intermediate A-6, which was of sufficient purity for the next step.

DIR Coupler I-5

Intermediate A-6 (2.0 g, 2.8 mMole), was dissolved in dry pyridine (30 mL) to which was added the sodium salt of phenyl mercaptotetrazole (0.61 g, 3.0 mMole). The resulting solution was stirred under nitrogen at room temperature for 3 hours. At the end of this period the reaction mixture was diluted with ethyl acetate (100 mL), and the ethyl acetate solution washed with 2N-HCl (2×50 mL), after which the product began to separate out of the organic layer. The organic layer and the precipatated solid were collected and concentrated under reduced pressure to yield the crude product. This material was suspended in diethyl ether and filtered off. The solid was washed with a little diethyl ether and air dried to yield DIR Coupler I-5, yield 1.9 g.

DIR Coupler I-6

Intermediate A-6 (2.0 g, 2.8 mMole), was dissolved in dry pyridine (30 mL) to which was added 2-nitro-4-((1-phenyl-1H-tetrazol-5-yl)thiomethyl)phenol (1.1 g, 3.34 mMole). The resulting solution was stirred under nitrogen at room temperature for 8 hours. At the end of this period the reaction mixture was diluted with ethyl acetate (100 mL), the ethyl acetate solution washed with 2N-HCl (2×50 mL), dried over magnesium sulfate, filtered and the solvent removed under reduced pressure. The residue was dissolved in a mixture of ethyl acetate:dichloromethane:heptane (15:20:65), and subjected to medium pressure column chromatography over silica gel using the same solvent in the elution. The fraction containg the product was collected and the solvent removed under reduced pressure to give DIR Coupler I-6, yield 1.0 g.

The above synthesis can be represented by the following scheme:

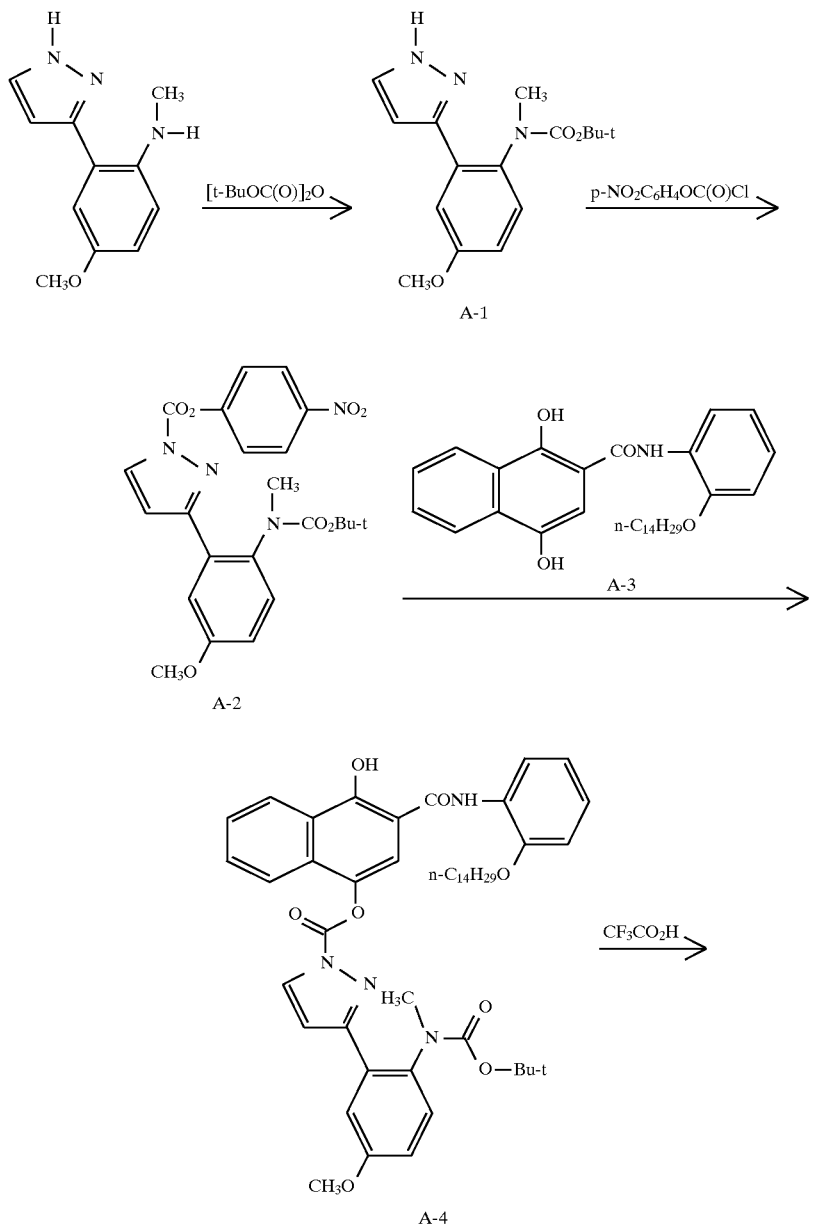

-continued

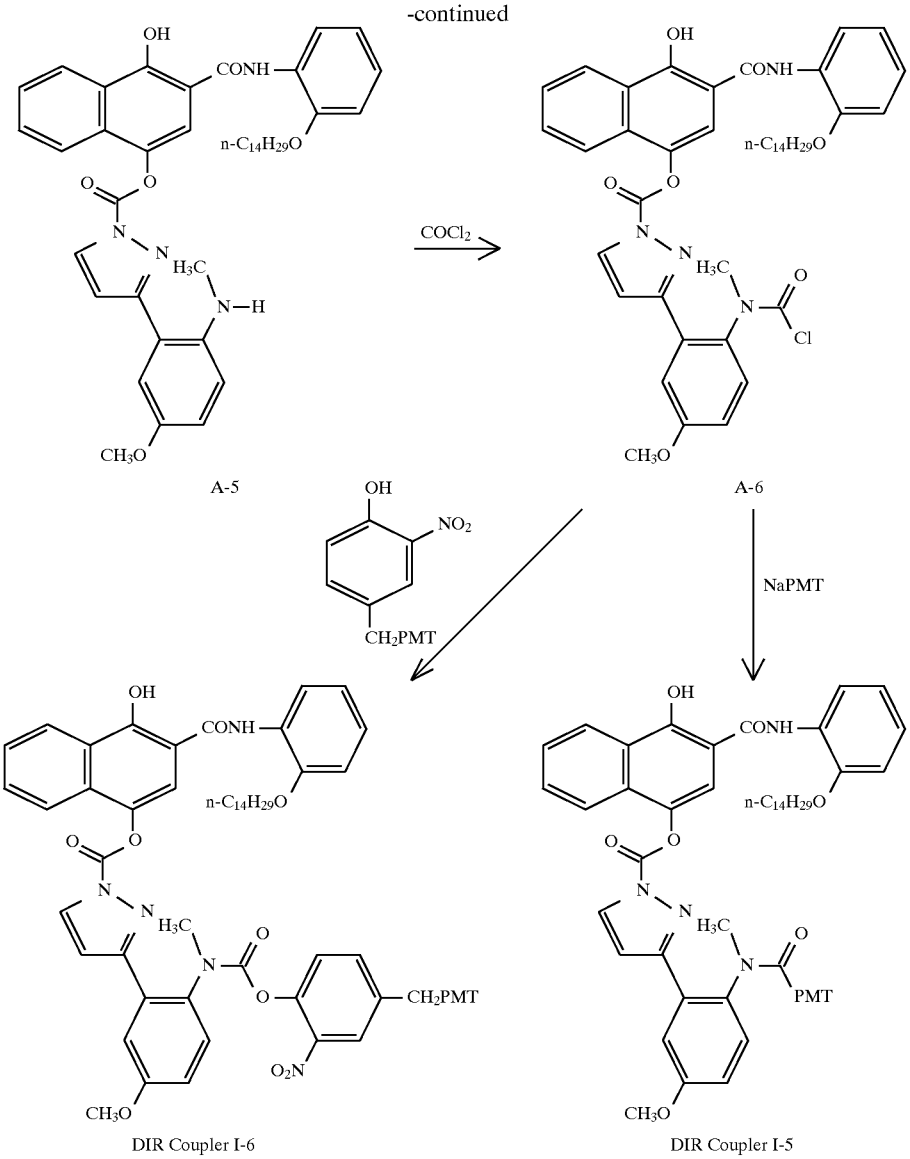

The following examples illustrate the practice of the invention. They are intended to be illustrative, and should not be construed as limiting the invention to the specific embodiments disclosed.

EXAMPLES

Photographic elements were prepared by coating the following layers on a cellulose ester film support (amounts of each component are indicated in mg/m$^2$):

| | |
|---|---|
| Emulsion layer 1: | Gelatin-2420; red sensitized silver bromoiodide (as Ag)-1615; yellow image coupler (Ye-1)-1290, dispersed in dibutyl phthalate. (RECEIVER LAYER) |
| Interlayer | Gelatin-860; didodecylhydroquinone-113 |
| Emulsion layer 2: | Gelatin-2690; green sensitized silver bromoiodide (as Ag)-1615; cyan image coupler (Cy-1)-768, |

-continued

| | |
|---|---|
| | dispersed in tritolyl phosphate; DIR coupler of Table 1 dispersed in N,N-diethyl-dodecanamide. (CAUSER LAYER) |
| Protective Overcoat | Gelatin-5380; bisvinylsulfonylmethyl ether at 2% total gelatin. |

Structures of couplers utilized in the Examples and not previously described are as follows:

Cyan Image Coupler, Cy-1:

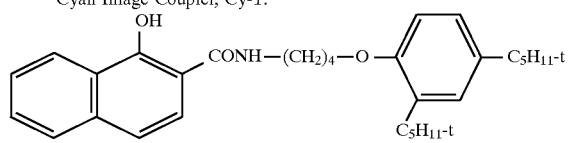

-continued

Yellow Image Coupler, Ye-1:

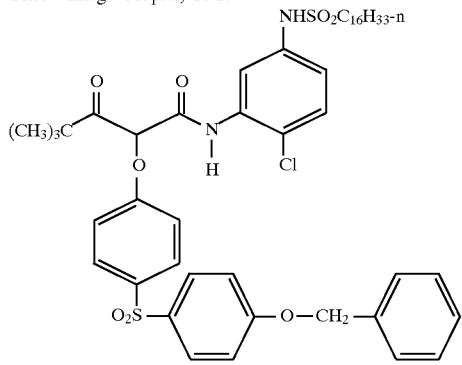

DIR Coupler: C-1

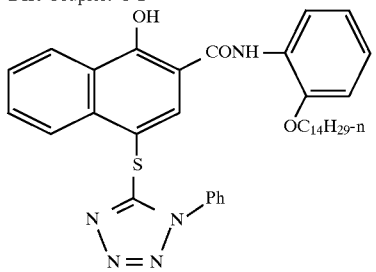

Strips of each element were exposed to green light through a graduated density step tablet, causer exposure, or through a 35% modulation fringe chart for sharpness measurements, and then developed for 3.25 minutes at 38° C. in the following color developer. Development was then stopped, and the elements washed, bleached, fixed, washed and dried.

| Color Developer | |
|---|---|
| Distilled water | 800 mL |
| Sodium Metabisulfite | 2.78 g |
| Sodium Sulfite, anhydrous | 0.38 g |
| CD-4' (color developer)* | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate | 2.41 g |
| Diethylenetriaminepentacetic acid, pentasodium salt (49% Soln.) | 8.43 g |
| Distilled water to 1 L | |
| Adjust pH to 10.0. | |

*CD-4' is a KODAK color developer in which the active component is 4-amino-3-methyl-N-ethyl-N-beta-hydroxy-ethylaniline sulfate.

Processed images were read with red light to determine the contrast ($\gamma$) and AMT acutance. Photographic effects were determined as follows: To determine acutance(AMT), a series of elements as described above containing no DIR coupler or varying levels of DIR coupler were exposed with green light. The contrast ($\gamma$) along the straight line portion of each elements' D log H curve was measured. A plot of log($\gamma$) versus amount of DIR coupler ($\mu$moles) was made for each element (each element containing a different DIR coupler). From these plots, the amount of DIR coupler needed to achieve log($0.5\gamma_o$) was read, where $\gamma_o$ represented the contrast of the element containing no DIR coupler. This value was recorded in the Table 1 as Amount* (* amount of DIR coupler need to reduce the contrast by 50%). In the same experiment, a plot of acutance versus log($\gamma$) was made for each element and from this plot the acutance at position log($0.5\gamma_o$) was read. These acutance values are shown in Table 1.

Acutance, as measured by AMT values and recorded in Table 1, are calculated using the following formula in which the cascaded area under the system modulation curve as shown in equation (21.104) on page 629 of the "Theory of the Photographic Process", 4th Edition, 1977, edited by T. H. James: AMT=100+66Log[cascaded area/2.6696M] wherein the magnification factor M is 3.8 for the 35 mm system AMT. The use of CMT acutance is described by R. G. Gendron in "An Improved Objective Method of Rating Picture Sharpness: CMT acutance" in the Journal of SMPTE, Vol. 82, pages 1009–12, (1973). AMT is a further modification of CMT useful for evaluating systems which include the viewing of a positive print made from a negative.

Interlayer interimage effects representing the degree of color correction capable of being obtained by practice of the invention were evaluated after the same series of photographic elements were exposed to white light. The log of the causer contrast($\gamma_c$) and the log of the receiver contrast ($\gamma_r$) were read for each of the DIR levels in the elements and a plot of log($\gamma_c$) versus log($\gamma_r$) was made. From this plot, ($\gamma_r$) was determined at log($0.5\gamma_o$), where log ($0.5\gamma_o$) was measured along the causer axis in the plot. The ratio ($\gamma_c$)/($\gamma_r$) was recorded in Table 1 as Interlayer Interimage.

TABLE 1

| Coupler | Amount* to Reduce $g_x$ 50% ($\mu$Moles/m²) | $\gamma$c | $\gamma$r | IIE $\gamma$c/$\gamma$r | AMT$_c$ (35 mm) |
|---|---|---|---|---|---|
| C-1 | 61.35 | 1.26 | 0.708 | 1.78 | 89.3 |
| I-5 | 109.37 | 1.26 | 0.646 | 1.95 | 90.4 |
| I-7 | 200.06 | 1.26 | 0.646 | 1.95 | 90.1 |

*Amount of the DIR coupler coated which is needed to reduce causer contrast ($\gamma$c) 50%.

It can be seen from Table 1 that the couplers utilized in this invention have superior interlayer interimage and acutance to the control coupler C-1.

The invention has been described in detail with particular reference to preferred embodiments thereof, but it will be understood that variations and modifications can be effected within the spirit and scope of the invention.

What is claimed is:

1. A photographic coupler represented by the formula:

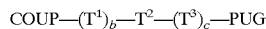

$$COUP—(T^1)_b—T^2—(T^3)_c—PUG$$

wherein

COUP is a coupler moiety having a coupling site to which $T^1$ is attached;

$T^1$ is a timing or linking group which releases from COUP during processing and which functions by electron transfer down a conjugated or unconjugated chain, or by a nucleophilic displacement reaction, to release $T^2$;

$T^2$ is a pyrazole timing or linking group which, after release from $T^1$, functions by a nucleophilic displacement reaction to release $T^3$ or PUG and is represented by the formula:

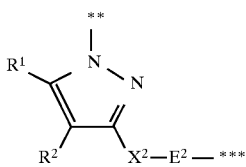

R¹ and R² are independently selected from hydrogen or halogen atoms, or an aliphatic, carbocyclic, carbamoyl, sulfamoyl, carbonamido, sulfonamido, alkoxycarbonyl, alkyl or arylketo, alkyl or arylsulfo, sulfo, hydroxy, acyl, nitro, cyano, amino, alkoxy, alkoxyalkyl, aryloxy, aryloxyalkyl, thioalkoxy, thioalkoxyalkyl, thioaryloxy, thioaryloxyalkyl or heterocyclic group, or R¹ and R², or R² and X² or E² may be bonded together to form a 5, 6, or 7 membered ring;

X² is a linking group which spatially relates a nitrogen atom of the pyrazole ring and E² so that upon displacement of T² from T¹, T² undergoes a nucleophilic displacement reaction with the formation of a three to eight membered ring and the cleavage of the bond between E² and PUG or T³;

E² is an electrophilic group which is attached to T³ and which is displaced therefrom by said nuclophilic displacement reaction after T² is displaced from T¹;

T³ is a timing or linking group attached to E² which is released therefrom after T² releases from T¹, and which functions by electron transfer down a conjugated or unconjugated chain, or by a nucleophilic displacement reaction, to release PUG;

b and c are independently selected from 0 or 1; and

PUG is a photographically useful group.

2. The photographic coupler of claim 1 wherein T¹ is

* * * * *